United States Patent [19]
Buecherl et al.

[11] Patent Number: 5,976,184
[45] Date of Patent: Nov. 2, 1999

[54] ARTIFICIAL HEART DRIVING DEVICE

[76] Inventors: Sebastian Buecherl, WAngenheimerstrasse 26, D-14193 Berlin; Joern Frank, Steinkirchener Strasse 22, D-13435 Berlin; Andreas Spiegelberg, Tempowerkring 4, D-21079 Hamburg; Igor Maximilian Sauer, Neue Kantstrasse 21, D-14057 Berlin, all of Germany

[21] Appl. No.: 08/875,974
[22] PCT Filed: Feb. 9, 1996
[86] PCT No.: PCT/DE96/00236
  § 371 Date: Sep. 25, 1997
  § 102(e) Date: Sep. 25, 1997
[87] PCT Pub. No.: WO96/24394
  PCT Pub. Date: Aug. 15, 1996

[30] Foreign Application Priority Data

Feb. 10, 1995 [DE] Germany ............... 195 05 512

[51] Int. Cl.⁶ ............................................. A61M 1/12
[52] U.S. Cl. ................................ 623/3; 417/534
[58] Field of Search ............................. 623/3; 600/16; 417/534–537; 415/900

[56] References Cited

U.S. PATENT DOCUMENTS

| | | | |
|---|---|---|---|
| 3,152,340 | 10/1964 | Fry et al. ................................. | 623/3 |
| 3,806,284 | 4/1974 | Jacobs ..................................... | 417/534 |
| 4,058,857 | 11/1977 | Runge et al. ............................. | 623/3 |
| 4,932,373 | 6/1990 | Carson ................................ | 123/197.4 |

FOREIGN PATENT DOCUMENTS

| | | | |
|---|---|---|---|
| 489931 | 1/1953 | Canada ................................. | 417/536 |
| 355869 | 1/1905 | France .................................. | 417/537 |
| 26 31 200 A1 | 1/1978 | Germany ............................ | 417/343 |
| 537074 | 12/1955 | Italy ..................................... | 417/536 |
| 885674 | 7/1959 | United Kingdom . | |

OTHER PUBLICATIONS

Kolff, An Artificial Heart inside the Body, Scientific American, 213(5), 38–46, Nov. 1965.

Vielberg, Intracorporeal Circulation Pump, Journal of Thoracic and Cardiovascular Surgery, 63(1), 143–148, Jan. 1972.

Byoung G. Min, Hee C. Kim, Sang H. Lee, Jong W. Kim, Jin T. Kim, In Y. Kim, Sung W. Kim, Paul D. Diegel and Don B. Olsen; "A Moving–Actuator Type Electromechanical Total Artifical Heart–Part I: Linear Type and Mock Circulation Experiments"; IEEE Transactions on Biomedical Engineering, vol. 37, No. 12; Dec. 1990.

*Primary Examiner*—David H. Willse
*Attorney, Agent, or Firm*—Marshall & Melhorn

[57] ABSTRACT

The invention concerns an artificial heart driving device having at least one blood chamber which is disposed in a pump housing and draws in and expels blood cyclically by means of a plurality of pressure plates which can be driven by a motor. The motor is directly connected to a drive gear or cam component. A movement component actuating the plurality of pressure plates engages with the drive gear or cam component and performs a reciprocating movement as the drive gear or cam component rotates.

16 Claims, 8 Drawing Sheets

ARTIFICIAL HEART DRIVING DEVICE

RELATED APPLICATIONS

This application is claiming the benefit, under 35 U.S.C. § 120 or § 365, of the international application filed Feb. 9, 1996 under 35 U.S.C. § 363, which was granted a Ser. No. of PCT/DE96/00236. The international application, Ser. No. PCT/DE96/00236 is hereby incorporated by reference.

BACKGROUND OF THE INVENTION

The invention relates to a drive device for an artificial heart according to the preamble of the main claim.

There is known from European Patent Application 0 531 856 a blood pump which operates in a pulsating manner, and in which there is disposed in the blood pump housing at least one piston driven from a coupling point on a triangular enclosed hypocycloid path, which periodically compresses a blood chamber and again releases it. One corner of the closed triangular hypocycloid path is aligned in the direction of the piston, piston movements arising which consist of a pre-stroke phase, a return stroke phase and a stationary stroke phase. This known blood pump is extremely complex in structure and comprises a large number of individual parts. The movement must be transmitted via a large number of bearings, so that many losses arise. Due to the complex structure, the lifespan of the drive of this pump is unsatisfactory.

U.S. Pat. No. 4,718,903 describes an artificial heart in which there is used as a drive a movable member, upon which pressure plates are secured, and which executes a rolling movement. The movable member has a bidirectional motor with motor housing and an epicycloid gear arrangement, the latter being disposed between the motor and one of two closure parts closing off the housing and rotating relative thereto, in such a way that the motor with housing executes the rolling movement led by guide means and the closure parts, which carry the pressure plates, execute a sliding movement. A reciprocating movement is achieved by reversing the polarity of the motor. Such an artificial heart is complex because of the epicycloid gear arrangement and has a large number of rotating parts. In addition, dead points are present because of the reversal of movement, and the end positions must be recognized for control of the motor.

OBJECT OF THE INVENTION

The object underlying the present invention is to provide a drive device for an artificial heart which is simple in structure and enables direct power transmission, while the lifespan is intended to be increased.

SUMMARY OF THE INVENTION

By virtue of the fact that the motor, rotating in one direction, is directly connected to a drive gear, and a movement component actuating a plurality of pressure plates and is in direct engagement with internal or external toothing and, upon rotation of a gearwheel, the movement component executes a reciprocating movement, there is a direct power transmission from the motor via the drive gear and the movement component to each pressure plate. Due to the direct power transmission the structure of the drive can be simplified, so that its lifespan is increased. This applies similarly to the solution with the features of the further independent claim.

Advantageous further developments and improvements are possible by means of the measures indicated in the sub-claims.

In an advantageous way, the movement component is in the form of an internal geared wheel, which has an internally geared oval, the internally geared oval being in engagement with the drive gear. By rotation of the drive gear, the internal geared wheel executes a reciprocating movement in the longitudinal direction with a degree of off-setting vertical to the longitudinal direction, and which is transmitted directly to the pressure plates.

By means of the guidance device, engagement is ensured between the drive gear and the internal geared wheel in a system of restricted guidance.

By virtue of the fact that a gel cushion is disposed on the pressure plates, the upward and downward movement of the pressure plates can be absorbed during the change of direction.

In a further preferred embodiment the movement component is in the form of a pendulum, which is pivotally mounted at one end and has at the other end a cam follower moving in the cam track, the pistons being pivotally attached to arms formed vertically to the pendulum. This embodiment also enables a simple structure and direct transmission of the drive power of the motor to the pistons without great loss.

BRIEF DESCRIPTION OF THE DRAWINGS

Embodiments of the invention given by way of example are shown in the drawings and will be described in more detail in the following. Shown are:

FIG. 1: schematic views of the first embodiment of the invention, FIG. 1a showing a cross-section along the section line A—A in FIG.1b, FIG. 1b showing an elevation along B—B in FIG. 1a, FIG. 1c showing an elevation along C—C in FIG. 1a and FIG. 1d showing an elevation along D—D in FIG. 1a;

DETAILED DESCRIPTION OF THE PREFERRED EMBODIMENTS

Figure 1A:
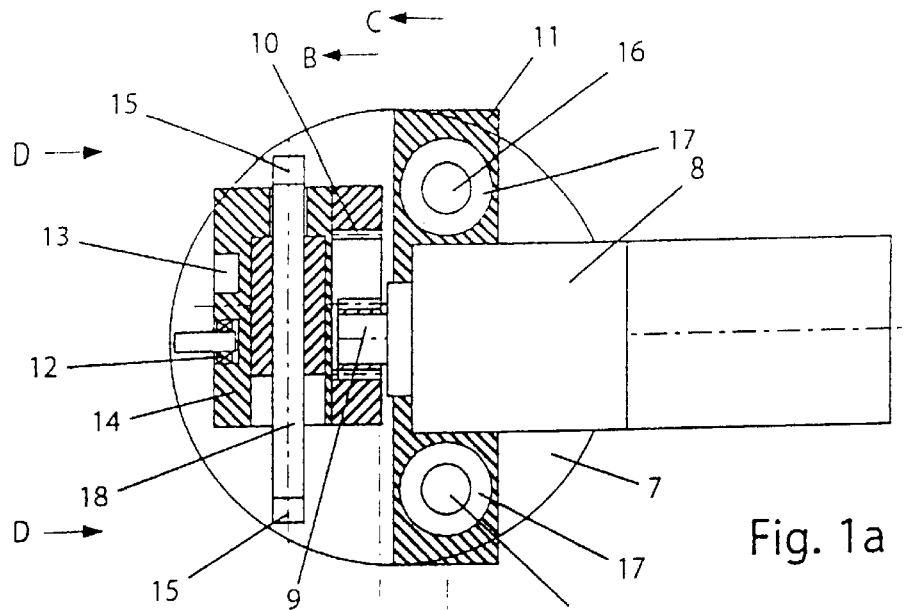
Figures 1B, 1C:
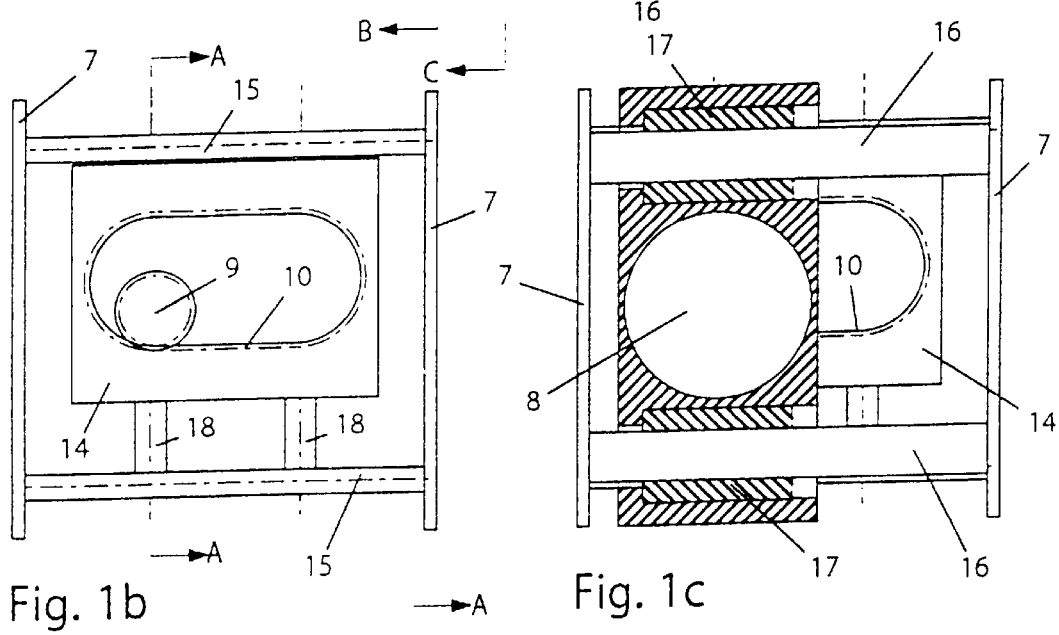
Figure 1D:
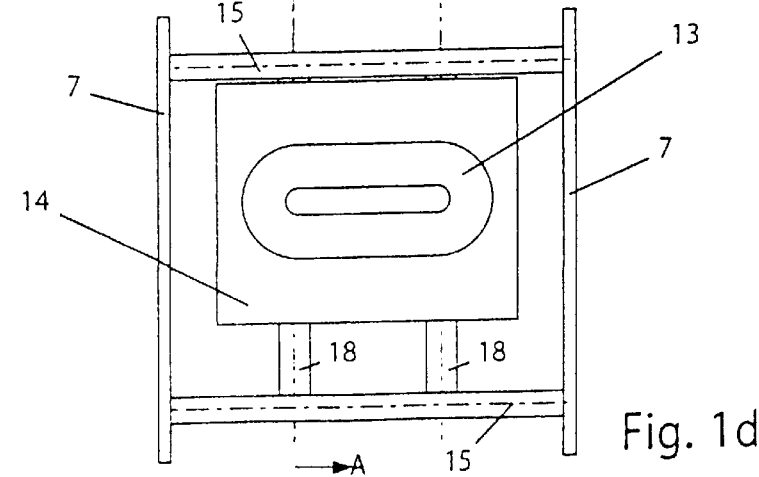
Figure 2A:
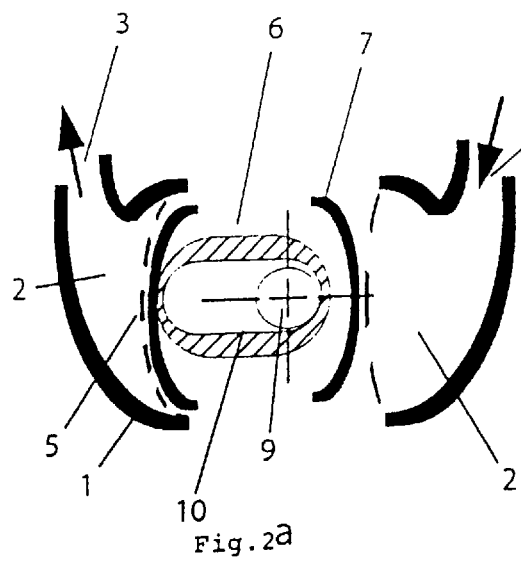
FIGS. 2a to 2f: the configuration of movement of the drive system according to the invention.
Figure 2D:
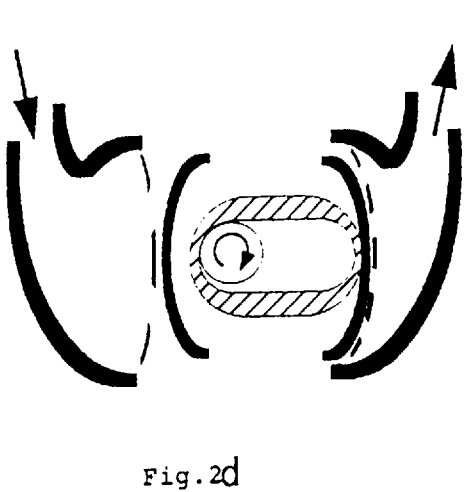
Figure 2B:
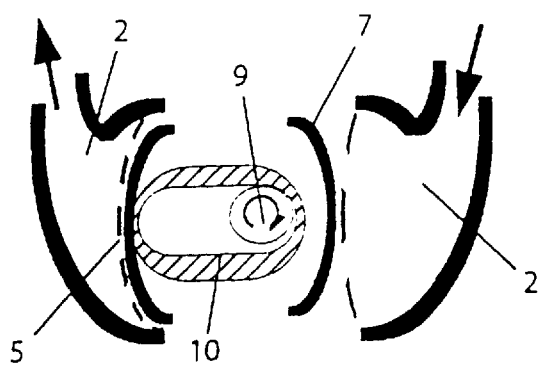
Figure 2E:
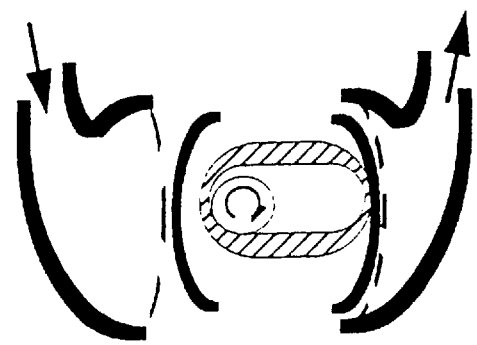
Figure 2C:
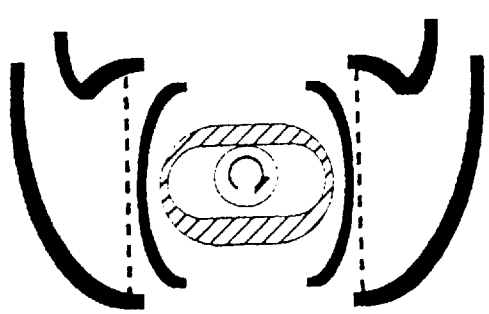
Figure 2F:
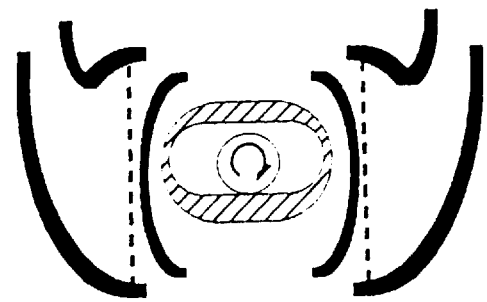
Figure 3A:
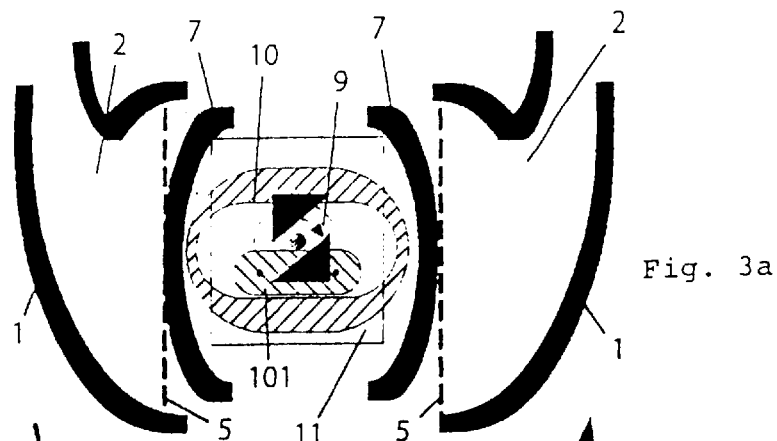
FIGS. 3a to 3d: schematic cross-sectional views of the drive system according to a second embodiment of the invention.
Figure 3B:
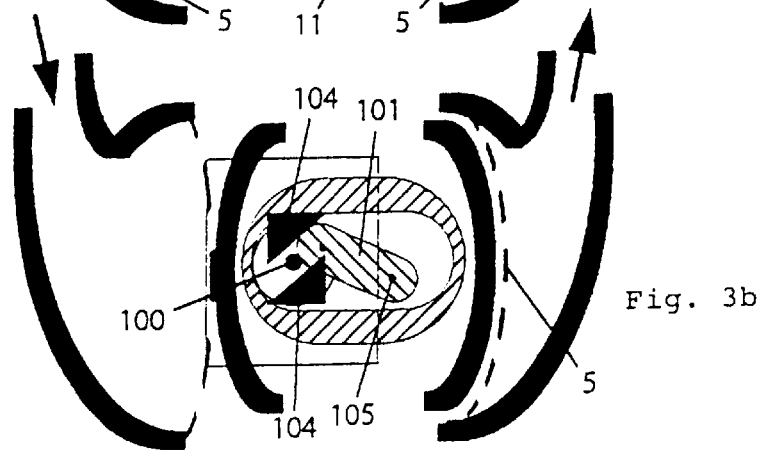
Figure 3C:
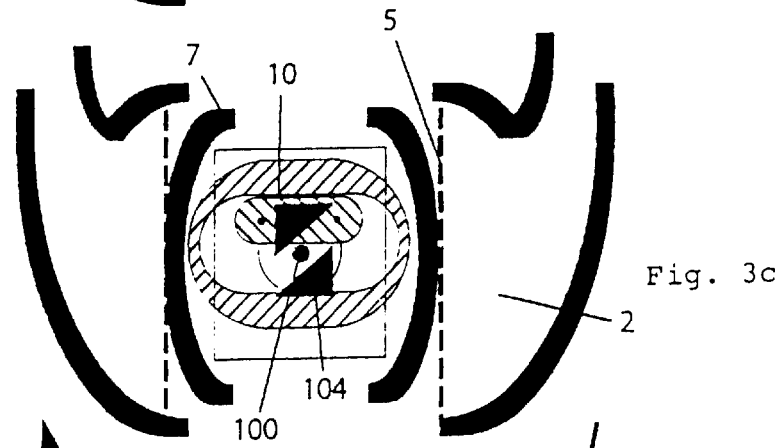
Figure 3D:
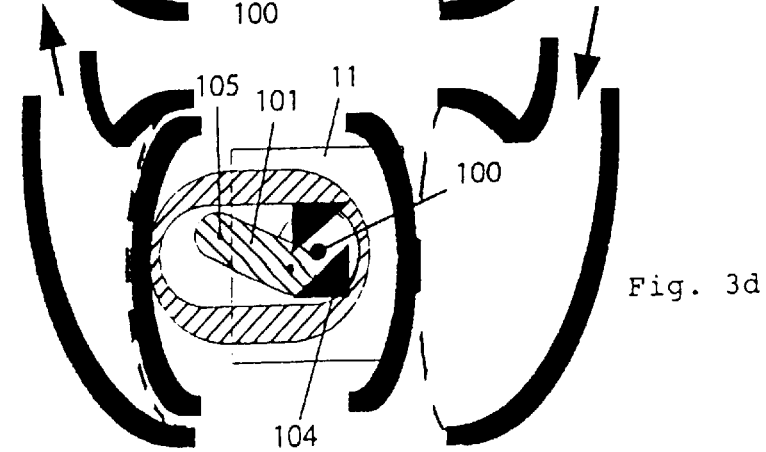

FIGS. 1a to 1d show various views of an embodiment given by way of example of a drive system for an artificial heart, and FIG. 2 shows a theoretical view of the configuration of movement of the essential portion of the drive with respect to a blood pump.

In FIG. 2, the pump housing is indicated by the reference number 1, which includes two blood chambers 2 with blood inlets and outlets 3, 4 respectively. The blood chambers are enclosed by membranes 5, preferably made of polyurethane, which are moved in accordance with the pump movement. Provided between the membranes 5 there is a drive system 6, which acts on pressure plates 7, which together with the membranes 5 form the pistons for altering the volume of the blood chambers 2.

According to FIGS. 1a–d, the drive system 6 has a motor 8, which may be in the form of a DC motor and rotates in one rotational direction and is mounted on a housing 11 or frame. Seated on the motor shaft is a drive gear 9, which engages with an internal geared wheel 10. The internal geared wheel 10 has an internally geared oval having the long sides lying parallel to one another and being respectively interconnected by arcs.

In order to ensure a permanent positive connection between the drive gear 9 and the internal gearing of the internal geared wheel 10, a guide device is provided, which includes a ball bearing 12 connected to the housing 11 and a guide track 13 in which the ball bearing 12 runs. The guide track 13, which is oval in shape, is adapted in its dimensions to those of the drive gear 8 and of the internally geared oval. The internal geared wheel 10 and the guide track 13 are formed from a block 14, which consists in the Figure of two rigidly interconnected portions.

The pressure plates 7 are interconnected via four longitudinal rods 15, 16, of which the parallel longitudinal rods 16 are displaceably guided in sleeves 17 rigidly connected to the housing 11. The longitudinal rods 15 are respectively rigidly connected to two cross bars 18, upon which the block 14 with the internal geared wheel 10 and the guide track 13 are displaceably mounted via sleeves 17.

The method of operation of the drive system for the artificial heart shown in FIG. 1 and FIG. 2 is as follows.

The drive gear 9 engaged with the internal gearing of the internal geared wheel 10 rotates for example according to FIG. 2 in a clockwise direction, the block 14 moving with the internal geared wheel 10 on the cross bars 18 and at the same time moving to the right. In this way the pressure plates 7 are pressed to the right together with the rods 15, 16, 18 and the block 14 with the internal geared wheel 10 against the membrane 5, so that the volume of the right-hand blood chamber 2 is reduced and, according to FIG. 2d, an evacuation takes place. The ball bearing 12 runs along the guide track 13 of block 14, ensuring the engagement between the gearwheels 9, 10. As the gearwheel 9 rotates further in accordance with FIG. 1c, the block 14 with the internal geared wheel 10 and the guide track moves back to the left until according to FIGS. 2a, b the pressure plate compresses the volume of the left-hand blood chamber to the minimum, evacuation in the left-hand chamber 2 taking place, while the right-hand chamber is filled.

As is to be seen on the right in FIG. 2, the internal geared wheel 10 also shifts together with the block 14 in an upward and downward direction, the perpendicular direction of movement respectively occurring at the moment of final systole. Due to this change of direction, friction occurs between the pressure plate 7 and the membrane 5. This can be prevented by providing a gel cushion between the pressure plate 7 and the membrane 5, which is disposed on the pressure plate and can absorb and compensate for the movements perpendicular to the longitudinal direction of the internal geared wheel. Other media may also be provided in order to ensure low-friction and low-wear power transmission.

Figure 4A:
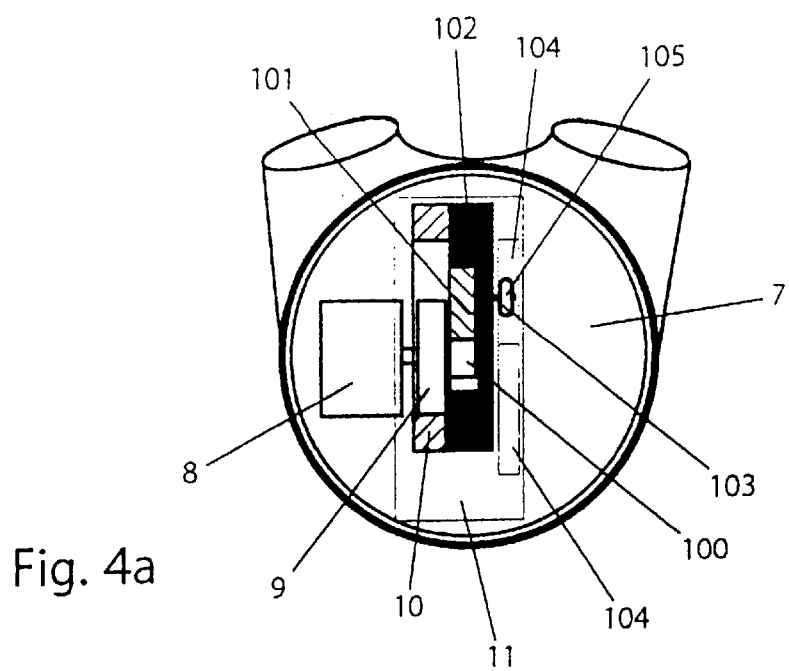
FIGS. 4a, 4b and 4c: schematic cross-sectional views in planes perpendicular to that of the embodiment in FIGS. 3a to 3d, FIG. 4a corresponding to FIG. 4c, but showing the drive system in slightly more detail.
Figure 4B:
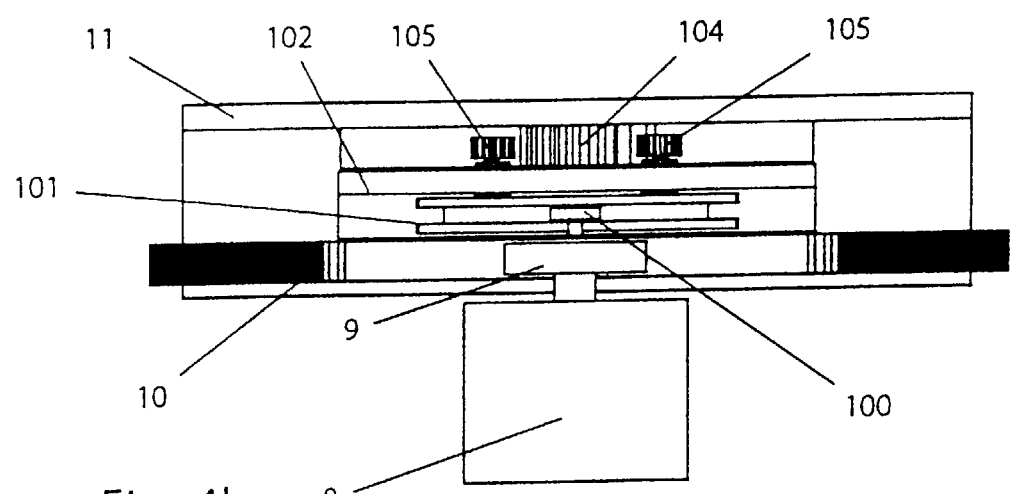
Figure 4C:
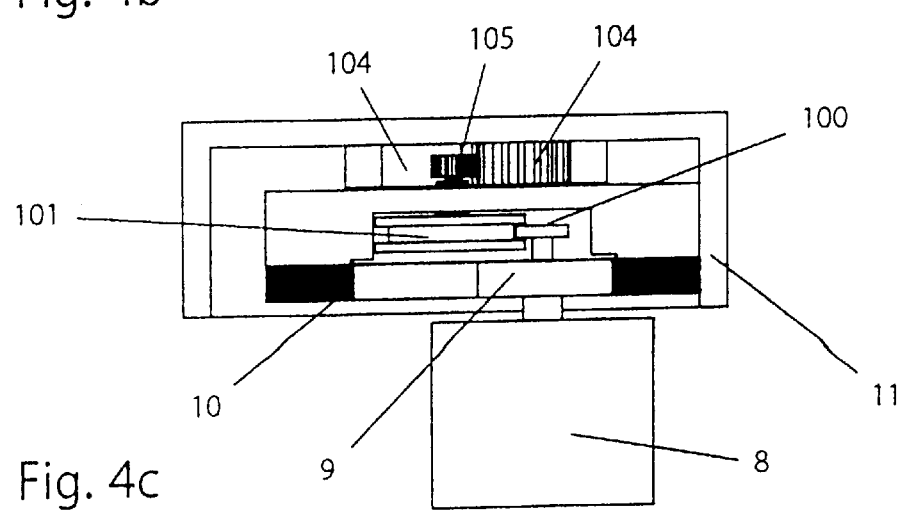

FIGS. 3 and 4 show a further embodiment of the drive system of an artificial heart, in FIG. 3 the configuration of movement corresponding to that in FIG. 2. The same reference numbers are used for identical parts. In this case, the guide device which ensures the positive connection between drive gear 9 and internal gearing of the internal geared wheel 10, has a roller 100 seated on the drive gear 9 or motor shaft, and a fitting block or fitting pad 101, which is adapted in its dimensions to those of the drive gear 9 and of the internal geared wheel 10. The fitting pad 101 is pivotally mounted with respect to the internal geared wheel 10. This pivotal mounting, as shown in FIG. 4, may be realised by having a frame or a support 102 rigidly connected to the internal geared wheel 10, curved grooves being provided in the support 102. Disposed on the fitting pad 101 are guide pins 103, which engage through curved grooves provided in the support, and predetermine the pivotal path or the pivotal range of the fitting pad 101 in accordance with the view in FIG. 3, the support 102 with the curved grooves not being shown in FIG. 3 for reasons of clarity. Naturally, the guide pins may also be replaced by ball bearings, which roll along the corresponding guide grooves. Disposed on the housing 11 as a "stationary portion" which supports the motor 8, are an upper and a lower deflector rails 104, and rollers 105 seated on the guide pins 103 roll along the deflector rails 104, in order to reinforce the movement of the drive gear 9 or of the internal geared wheel 10 in the arcuate region. Fitting pad 101 and internal geared wheel 10 are so disposed that, in the final systole, the fitting pad 101 is forced by the deflector rails to change its position respective to the internal oval. While the drive gear 9 is running through the semi-circular segment of the internal oval, the fitting pad 101 tilts on to the other broad side of the oval and thus ensures engagement of the drive gear 9 and of internal geared wheel 10 when running back along the oval.

Otherwise the method of operation of this embodiment corresponds to that in FIG. 1.

Figure 5A:
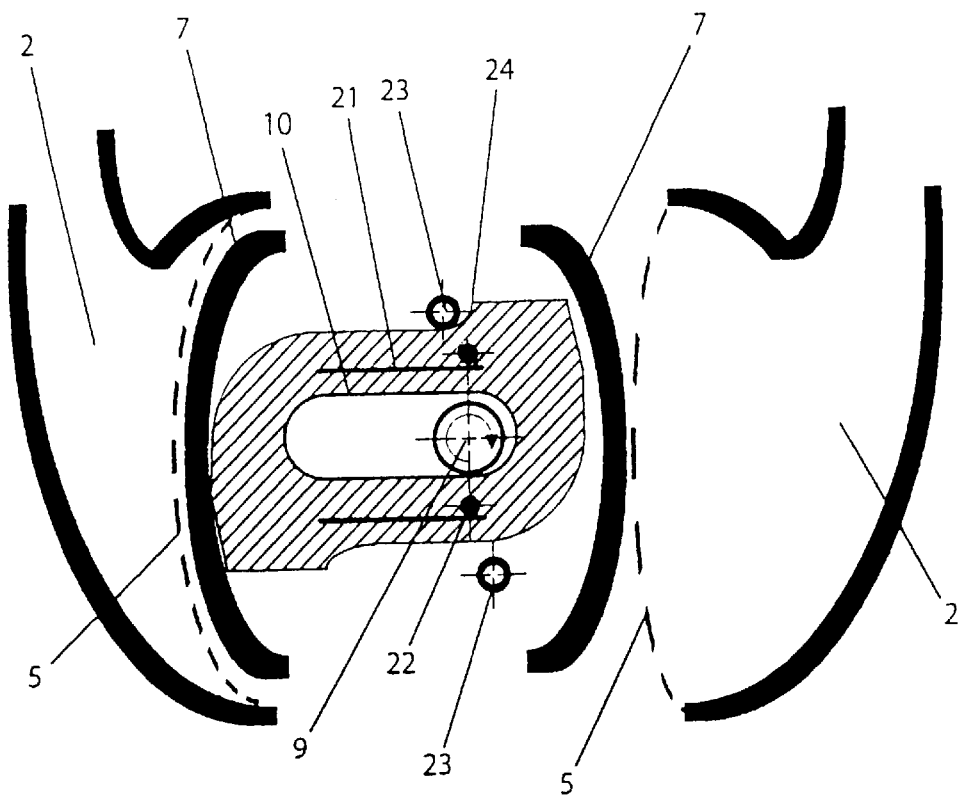
FIGS. 5a and 5b: schematic cross-sectional views through a drive system according to a third embodiment of the invention.
Figure 5B:
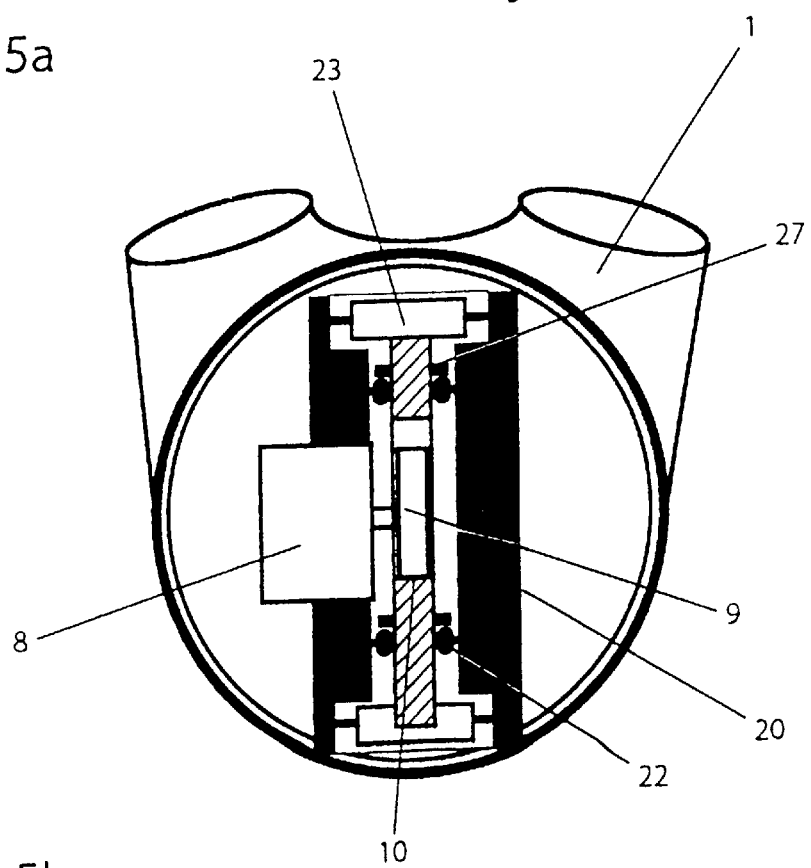

FIGS. 5a and 5b show a further embodiment in which the restricted guidance of the drive gear 9 is designed in a different manner with respect to the internal geared wheel 10. Here also, identical parts are provided with identical reference numbers in accordance with FIGS. 1 to 4. As is to be seen from FIG. 5b, a housing 20 is provided, which can likewise serve to accommodate the motor 8. The internal geared wheel 10 has, parallel to the long sides of the internally-geared oval respectively above and below it, guide rails 21 on either side. Associated with these guide rails 21 are rollers 22, which are disposed on axes rigidly connected to the housing 20. In order to reinforce the deflecting movement in the arcuate region of the internally-geared oval, deflector rollers 23 are connected to the housing, which roll along the periphery of the internal geared wheel 10, upon which two cam tracks 24 are respectively provided.

As FIG. 5a shows, the internal geared wheel is in a position in which the volume of the left-hand blood chamber 2 is reduced. In this case the rollers 22 connected to the housing roll above the guide rails 21 along the internal geared wheel 10. The upper deflector roller 23 runs along the upper cam track 24 and, in order to guide the roller 22 around the guide rails 21 and to ensure restricted guidance around the arcuate region, the cam track 24 is slightly curved at the end in such a way that the deflector roller 23 presses the internal geared wheel 10 downwards, and in further continuation of the movement, the internal geared wheel 10 is slowly pushed to the right, the lower cam track 24 rolling on the lower roller 23 and the rollers 22, seen in FIG. 5a, run along under the guide rails 21.

In a further embodiment, the rollers 22 may be disposed on the internal geared wheel 10 and the guide rails 21 may be provided on the housing.

Figure 6A:
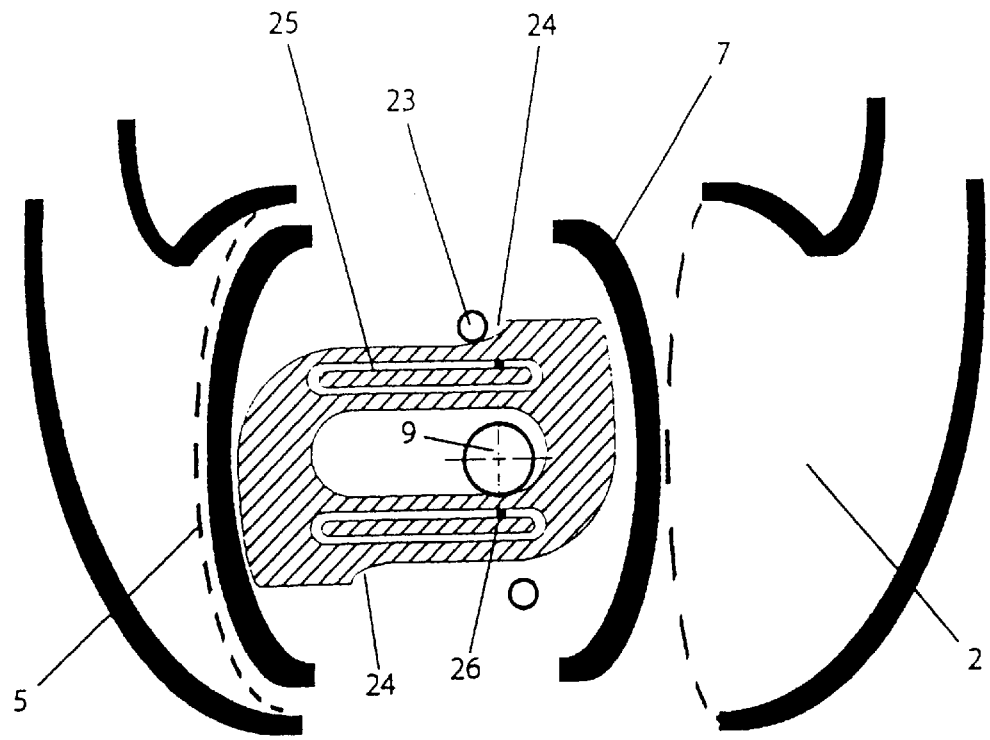
FIGS. 6a and 6b: schematic cross-sectional views through a drive system according to a fourth embodiment of the invention.
Figure 6B:
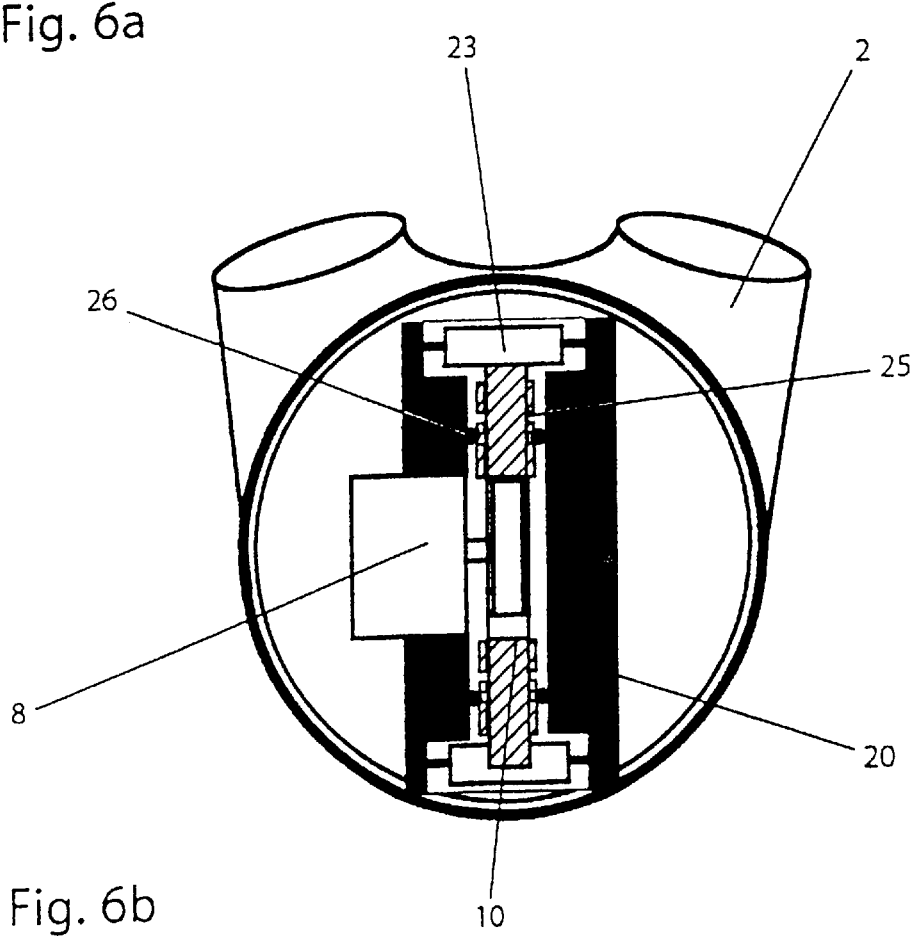

FIGS. 6a and 6b show a similar embodiment to that in FIGS. 5a and 5b; in this case however there are provided in the internal geared wheel 10 continuous guide grooves 25 above and beneath the internally geared oval in accordance with the path of the drive gear 9 in the internally geared oval, instead of the roller 22 and the guide rails 21. Corresponding guide grooves can be disposed in the housing 20. Between the housing 20 and the guide grooves 25 there run in the internal gearwheel balls 26 which, together with the deflector rollers 23 and the cam tracks 24, form the restricted guidance system for the internal geared wheel 10. Otherwise the method of operation is the same as that in the embodiment according to FIGS. 5a and 5b.

In the embodiments described above, the internal geared wheel 10 has been described as an internally geared oval. In its place, however an internally geared aperture may be used with an optional peripheral line defining the desired movements.

In a further embodiment which is not shown, an externally geared wheel with external toothing can be provided, the drive gear 9 running on the external toothing. A guide device corresponding to the internal geared wheel ensures engagement between the external gearing and the drive gear.

Figure 7:
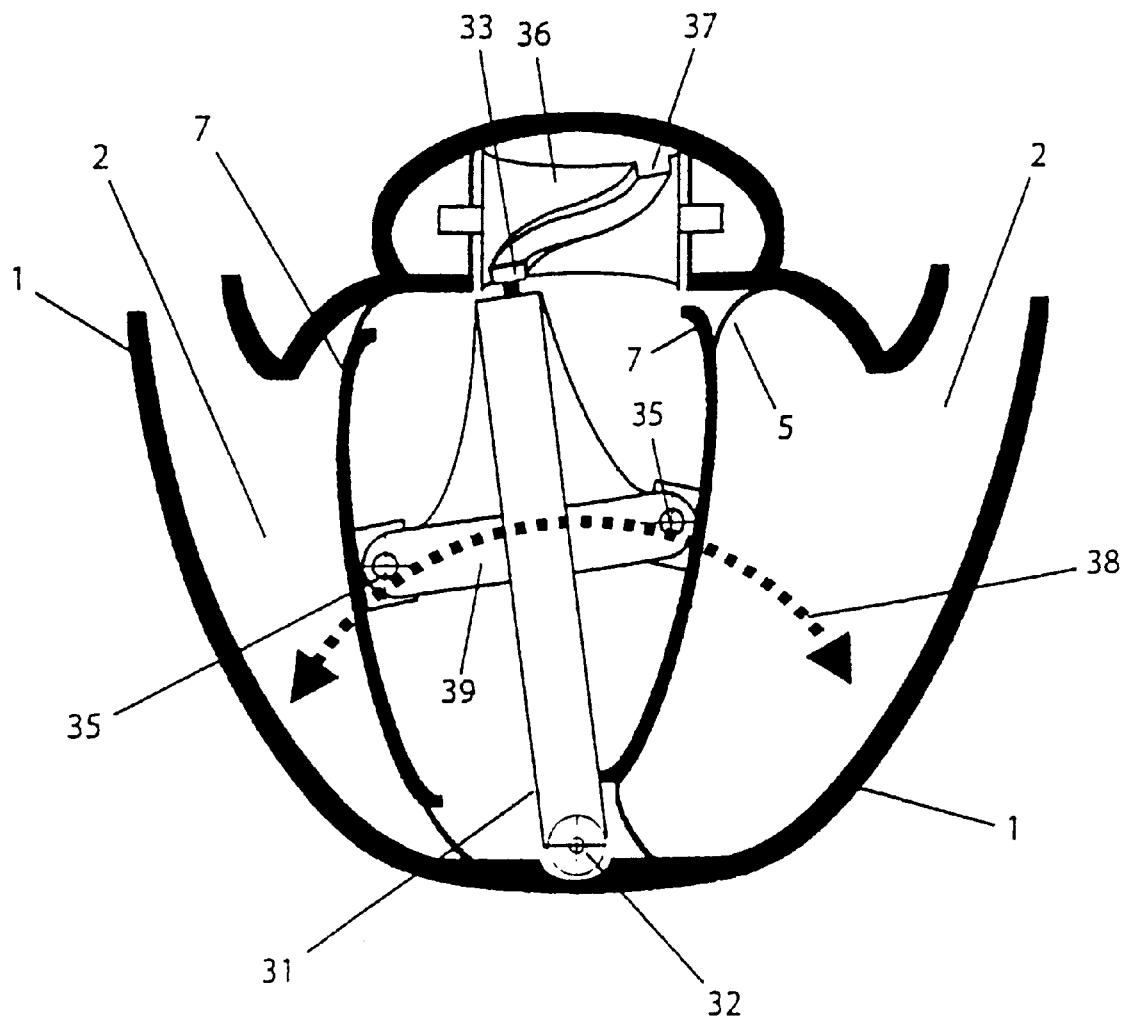
FIG. 7: a schematic cross-sectional view through a drive system according to a fifth embodiment of the invention.
Figure 8:
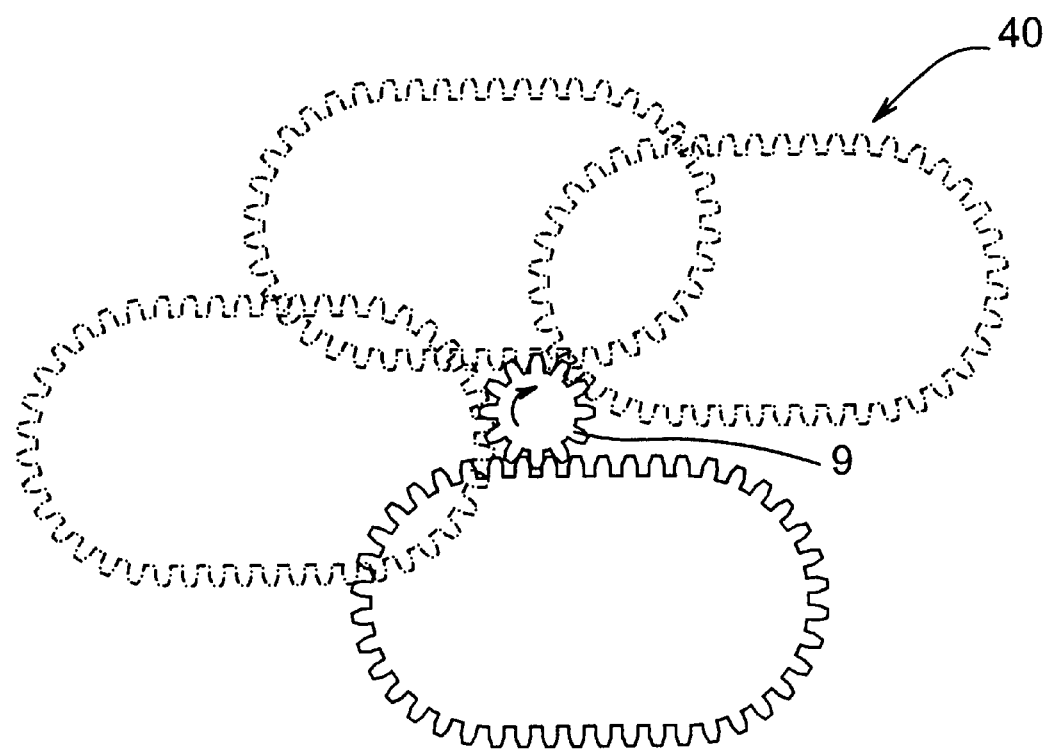

FIG. 7 shows a further embodiment in which the movement components actuating the piston of a drive system for the artificial heart is in the form of a pendulum 31. The rod-shaped pendulum 31 is pivotally mounted at one end in the pump housing 1 not shown in detail, via a joint 32. Provided at the other end is a cam follower 33 in the form of a roller. The rod-shaped pendulum 31 is connected to lateral rod-shaped extensions 39, on the ends of which are disposed the pressure plates 7 via connecting joints 35. In this embodiment the membrane 5 is stationarily connected to the pressure plate 7. The cam follower 33 runs along a cam track 37 provided in a rotary drum 36 with an integrated motor on its periphery, the cam track 37 being so formed that, upon a rotation of the drum 36, the pendulum executes a reciprocating movement in accordance with arrow 38 due to the restricted guidance of the cam follower 33 in the cam track 37. The blood chamber 2 is filled or emptied in accordance with the volume changes brought about by the pendulum movements.

We claim:

1. A drive device for an artificial heart with blood chambers disposed in a pump housing, said chambers cyclically drawing in and expelling blood by means of pressure plates driveable by a motor, comprising:

a motor rotating in a single direction;

a drive gear drivingly coupled to said motor;

a movement component with internal or external gear teeth in direct meshing engagement with the drive gear; and said plurality of pressure plates being connected with the movement component;

the movement component upon rotation of the drive gear executing a reciprocating movement and directly actuating the plurality of pressure plates.

2. The drive device according to claim 1, wherein the movement component has an internal geared wheel which engages with the drive gear and which is in the form of an internally geared aperture with a predetermined peripheral line.

3. The drive device according to claim 2, wherein the internal geared wheel is in the form of an internally geared oval.

4. The drive device according to claim 2, wherein the plurality of pressure plates are interconnected via a plurality of longitudinal rods and a plurality of cross bars, a block including the internal geared wheel is displaceably guided on the plurality of cross bars, and at least one of the plurality of longitudinal rods is displaceably mounted in a housing accommodating the motor.

5. The drive device according to claim 2, wherein a guide device is provided, which ensures an engagement between the drive gear and the internal geared wheel.

6. The drive device according to claim 5, wherein the guide device is designed as a plurality of guide rails disposed parallel to a longitudinal direction of the internally geared aperture of the internal geared wheel, and as a plurality of ball bearings rolling on the plurality of guide rails, the plurality of guide rails being disposed on a stationary housing and the plurality of ball bearings on the internal geared wheel, or vice versa.

7. The drive device according to claim 5, wherein the guide device is designed as a plurality of guide grooves provided in the internal geared wheel, each having a shape according to the shape of the internally geared aperture, and a plurality of rolling members in connection with a housing rolling along the plurality of guide grooves.

8. The drive device according to claim 5, wherein the guide device is in the form of an oval fitting pad, and as a ball bearing disposed on an axis of the drive gear, the ball bearing rolling on the external periphery of the fitting pad and the fitting pad being pivotally connected to the internal geared wheel.

9. The drive device according to claim 8, wherein the guide device has a plurality of deflector members which reinforce a restricted guidance system between the drive gear and the internal geared wheel.

10. The drive device according to claim 9, wherein the plurality of deflector members are designed as a plurality of deflector rails connected to a housing, and as a plurality of track rollers connected to the fitting pad.

11. The drive device according to claim 5, wherein the guide device has a plurality of deflector members which reinforce a restricted guidance system between the drive gear and the internal geared wheel.

12. The drive device according to claim 11, wherein the plurality of deflector members are designed as a plurality of deflector rollers connected to a housing, and as a plurality of cam tracks disposed on an external periphery of the internal geared wheel, each of the deflector rollers respectively rolling along the cam track associated therewith.

13. A drive device for an artificial heart with blood chambers disposed in a pump housing, said chambers cyclically drawing in and expelling blood by means of a pressure plate driveable by a motor, comprising:

a rotary drum;

a motor rotating in a single direction integrated into the drum;

a cam member having a cam track on the periphery of the drum being directly connected to the motor;

a pendulum-like movement component engaging with the cam member and upon rotation of the cam member executing a reciprocating movement; and a plurality of pressure plates being connected to the pendulum-like movement component.

14. The drive device according to claim 13, wherein a first end of the pendulum-like movement component is stationarily and pivotally mounted, and a second end has a cam follower, which rolls along the cam member having the form of a cam track and causes a pendulum movement, and on the pendulum-like movement element laterally extending extensions are disposed which are pivotally connected to the plurality of pressure plates.

15. The drive device according to claim 14, wherein the cam track is formed continuously on the circumferential surface of the drum which is driven by the motor.

16. A drive device for an artificial heart with blood chambers disposed in a pump housing, said chambers cyclically drawing in and expelling blood by means of pressure plates driveable by a motor, comprising:

- a motor rotating in a single direction;
- a drive gear drivingly coupled to said motor;
- a movement component with external gear teeth in direct meshing engagement with the drive gear;
- said plurality of pressure plates connected with the movement component; and
- a guide device ensuring engagement between the drive gear and the movement component;

the movement component upon rotation of the drive gear executing a reciprocating movement and directly actuating the plurality of pressure plates.

* * * * *